United States Patent [19]

Barnes et al.

[11] Patent Number: 5,500,992
[45] Date of Patent: Mar. 26, 1996

[54] METHOD OF MAKING STRESS RELIEVED COUNT PROBE

[75] Inventors: Thomas L. Barnes, Sunrise; James W. Colburn, Margate; Catherine L. Danial, Coconut Creek; William R. Jones, Jr., Hialeah; Millard D. Longman, Coral Springs, all of Fla.

[73] Assignee: Abbott Laboratories, Abbott Park, Ill.

[21] Appl. No.: 407,790

[22] Filed: Mar. 20, 1995

Related U.S. Application Data

[63] Continuation of Ser. No. 173,524, Dec. 23, 1993, abandoned.

[51] Int. Cl.⁶ .................................................. B23P 19/02
[52] U.S. Cl. ........................ 29/525; 264/346; 324/71.4; 73/861.41; 73/865.5
[58] Field of Search ............................ 29/525; 324/71.4; 264/346; 73/861.41, 865.5

[56] References Cited

U.S. PATENT DOCUMENTS

| | | |
|---|---|---|
| 1,585,542 | 5/1926 | Henry ..................................... 264/346 |
| 3,122,431 | 2/1964 | Coulter et al. . |
| 3,266,526 | 8/1966 | Berg . |
| 3,361,965 | 1/1968 | Coulter et al. . |
| 3,395,343 | 7/1968 | Morgan et al. . |
| 3,395,344 | 7/1968 | Bader . |
| 3,444,464 | 5/1969 | Coulter et al. . |
| 3,515,884 | 6/1970 | Imadate . |
| 3,539,919 | 11/1970 | Hogg . |
| 3,554,037 | 1/1971 | Berg . |
| 3,614,607 | 10/1971 | Schoen . |
| 3,628,140 | 12/1971 | Hogg et al. . |
| 3,638,677 | 2/1972 | Baccarini . |
| 3,648,158 | 3/1972 | Parker . |
| 3,714,565 | 1/1973 | Coulter et al. . |
| 3,739,258 | 6/1973 | Karuhn et al. . |
| 3,746,976 | 7/1973 | Hogg . |
| 3,771,058 | 11/1973 | Hogg . |
| 3,779,254 | 12/1973 | Linskey ............................... 131/198.1 |
| 3,779,279 | 12/1973 | Schön .................................... 324/71.4 |
| 3,783,376 | 1/1974 | Doniguian . |
| 3,859,012 | 1/1975 | Hogg . |
| 3,864,628 | 2/1975 | Klass et al. . |
| 3,902,115 | 8/1975 | Hogg et al. . |
| 3,939,409 | 2/1976 | Hogg . |
| 3,958,177 | 5/1976 | Reeves et al. . |
| 3,976,429 | 8/1976 | Ginsberg . |
| 4,014,611 | 3/1977 | Simpson et al. . |
| 4,140,966 | 2/1979 | Godin et al. . |
| 4,157,498 | 6/1979 | Johnson . |
| 4,325,913 | 4/1982 | Wardlaw . |
| 4,395,676 | 7/1983 | Hollinger et al. . |
| 4,484,134 | 11/1984 | Halloran . |
| 4,491,786 | 1/1985 | Godin . |
| 4,710,021 | 12/1987 | Von Behrens . |
| 4,730,155 | 3/1988 | Hogg . |
| 4,760,328 | 7/1988 | Groves . |
| 4,853,618 | 8/1989 | Holley . |
| 5,041,181 | 8/1991 | Brackett et al. ......................... 156/84 |
| 5,158,732 | 10/1992 | Sanitate .................................. 264/346 |

OTHER PUBLICATIONS

International Search Report for PCT/US94/13452 corresponding to US 08/173,524.

Primary Examiner—David P. Bryant
Attorney, Agent, or Firm—Mark C. Bach

[57] ABSTRACT

A method of making a count probe for counting particles comprises the following steps. A count wafer is formed along with a core member having an opening for accepting the count wafer. The count wafer is applied to the opening in the core member to form an interference fit between the count wafer and the core member. After application of the count wafer to the opening in the core member, the core member is annealed to relieve stress in the core member.

2 Claims, 5 Drawing Sheets

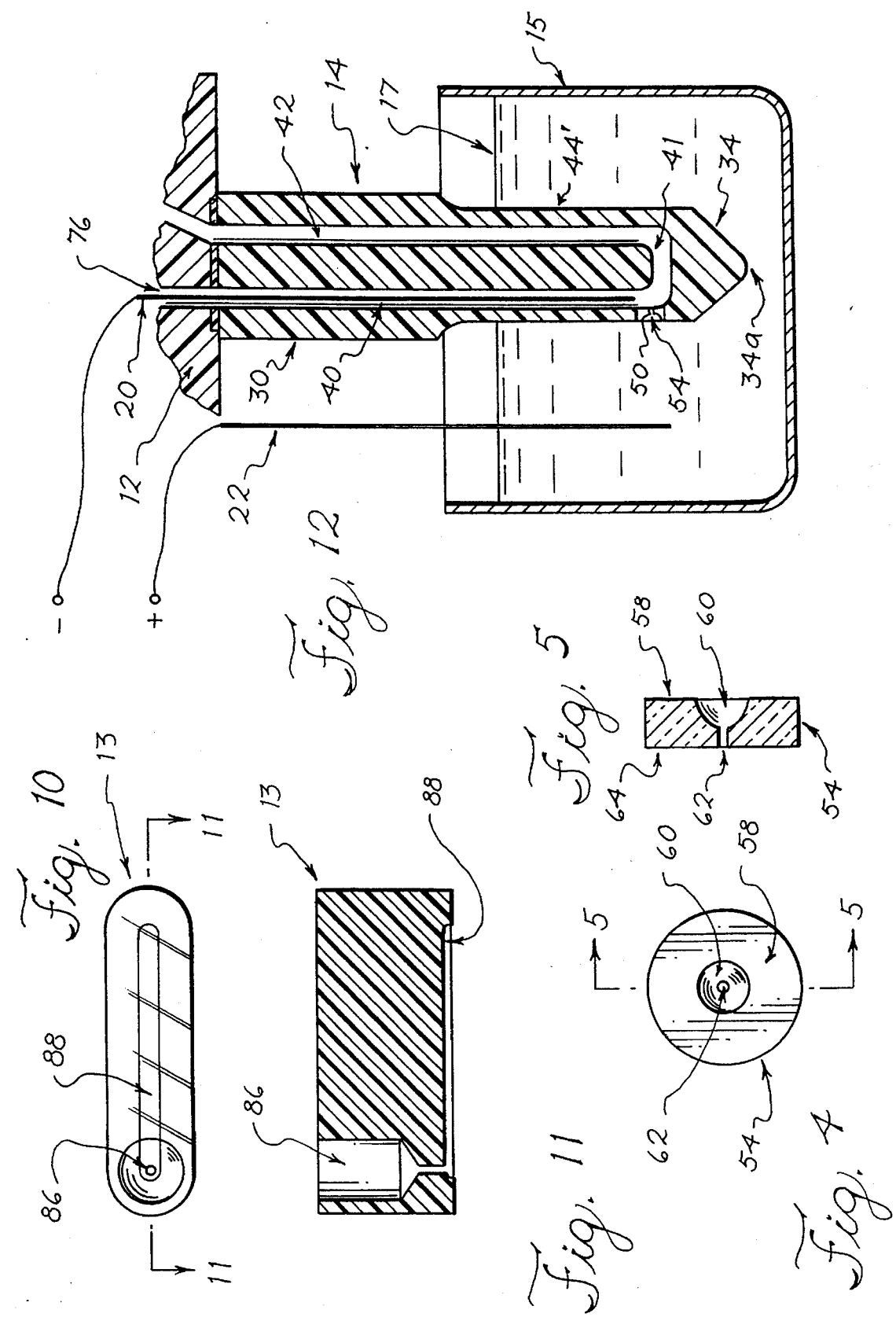

METHOD OF MAKING STRESS RELIEVED COUNT PROBE

This application is a continuation of application Ser. No. 08/173,524 filed on Dec. 23, 1993, now abandoned.

FIELD OF THE INVENTION

Embodiments of the present invention are directed to the field of particle analysis systems and, in particular, to methods of making a stress relieved count probe.

DESCRIPTION OF THE PRIOR ART

In the particle analysis field, analysis of liquid samples may involve aspiration of liquid from a sample through a conduit having a metered aperture at an immersed end. A typical particle analyzer includes three basic components: a sample vessel, a liquid flow system, and a sensor. U.S. Pat. No. 5,094,818 to Longman et al., issued 10 Mar., 1992, which is incorporated herein by reference, describes one type of particle analyzer. The particle analyzer moves suspended biological or industrial particles from the sample vessel to the sensor via the liquid flow system. The suspended particles are moved through the sensor, and the sensor detects, counts and sizes the particles.

There are many types of sensors. Impedance sensors detect the change in resistance of an aperture as a particle passes through the aperture. The aperture is constructed such that particles pass through the aperture substantially one at a time.

Impedance sensors generally include a probe assembly with a count wafer. The probe assembly has a counterbore in which the count wafer is mounted. The count wafer is held in place by adhesive materials such as glue and the like. Using an adhesive to mount the count wafer to the probe assembly may create several problems. The material comprising the wafer and the probe material are different such that the adhesive is unable to hold the count wafer properly in place. Subsequently, the adhesive bond may fail.

The adhesive joint must survive under pressure in an immersed environment. Under these conditions, adhesives may fail with an adhesion failure. An adhesion failure occurs between the adhesive and the substrate. An impedance sensor has at least two substrates: the count wafer and the probe assembly. Additionally, there is a relatively small surface area on the sensor which is available for the adhesive. Because the available surface area is so small, it is extremely sensitive to surface preparation and proper mixing of the adhesive so it remains air and moisture free.

It is desirable to provide a method of mounting a count wafer to a probe assembly which provides increased flexibility. Such a method would also preferably not be subject to the above-discussed disadvantages.

SUMMARY OF THE INVENTION

A method of making a count probe for counting particles comprises the following steps. A count wafer is formed along with a core member having an opening for accepting the count wafer. The count wafer is applied to the opening in the core member to form an interference fit between the count wafer and the core member. After application of the count wafer to the opening in the core member, the core member is annealed to relieve stress.

An example of the annealing method comprises the following steps. The core member is moved from ambient temperature to a first temperature within a first time period. The core member is maintained at the first temperature for a second time period. The core member is moved to a second temperature within a third time period. The core member is maintained at the second temperature for a fourth time period. The core member is moved to a third temperature within a fifth time period. The core member is maintained at the third temperature for a sixth time period. The core member is moved to ambient temperature within a seventh time period.

Another example of the annealing method comprises the following steps. The core member is moved from ambient temperature to a first temperature within a first time period. The core member is maintained at the first temperature for a second time period. The core member is moved to a second temperature within a third time period. The core member is maintained at the second temperature for a fourth time period. The core member is moved to a third temperature within a fifth time period. The core member is maintained at the third temperature for a sixth time period. The core member is moved to a fourth temperature within a seventh time period. The core member is maintained at the fourth temperature for an eighth time period. The core member is moved to ambient temperature within a ninth time period.

BRIEF DESCRIPTION OF THE DRAWINGS

FIG. 4 illustrates a front view of a count wafer which may be used with the probe assembly of FIG. 3.

FIG. 5 illustrates a cross-sectional view of the count wafer shown in FIG. 4 taken along lines 6—6.

FIG. 10 illustrates a top view of a plug of the counting apparatus shown in FIG. 1.

FIG. 11 is a cross-sectional view of the plug shown in FIG. 10.

FIG. 12 illustrates a cross-sectional view of a count probe of the counting apparatus shown in FIG. 1 immersed in a reservoir containing a liquid suspension of particles to be analyzed.

DETAILED DESCRIPTION OF THE PREFERRED EMBODIMENTS

For the sake of clarity, the construction of probe assemblies, which may be manufactured according to methods utilizing teachings of the present invention, will be discussed first. However, it is to be understood that the methods disclosed and claimed herein may be used to manufacture other probe assemblies and other similar products in addition to the particular constructions described in detail in the following paragraphs.

Figure 1:
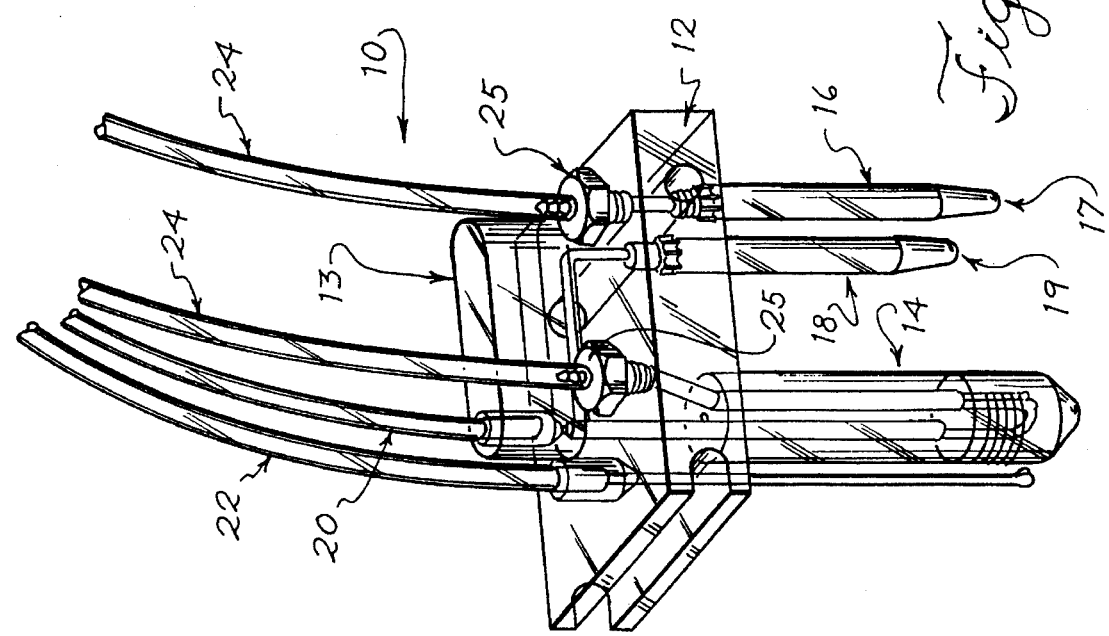
FIG. 1 illustrates a probe assembly which may be constructed utilizing the teachings of a method of the present invention.

A probe assembly 10, illustrated in FIG. 1, includes a base 12, a plug 13, count probe 14, a waste probe 16, a fill probe 18, electrodes 20 and 22, connection tubing 24 and connection fitting 25. The assembly 10 is used in conjunction with a vessel (not shown) having two separate reservoirs. In one application, a sample, such as a biological or industrial suspension of particles to be analyzed, is contained in one reservoir while the other reservoir contains a reagent solution. Depending on the type of analysis to be performed, the sample may be treated before being added to the reservoir. When the reservoirs are filled with their respective solutions, the reservoirs are raised to the probe assembly 10 so that the count probe 14 aligns with the reservoir containing the sample to be analyzed and the waste and fill probes 16 and 18 align with the reservoir containing the reagent solution. The remaining portion of the assembly 10, including the base 12 and plug 13 is not immersed in the vessel. Individual components of the probe assembly 10 will now be described in detail with reference to FIGS. 2–12.

Figure 3:
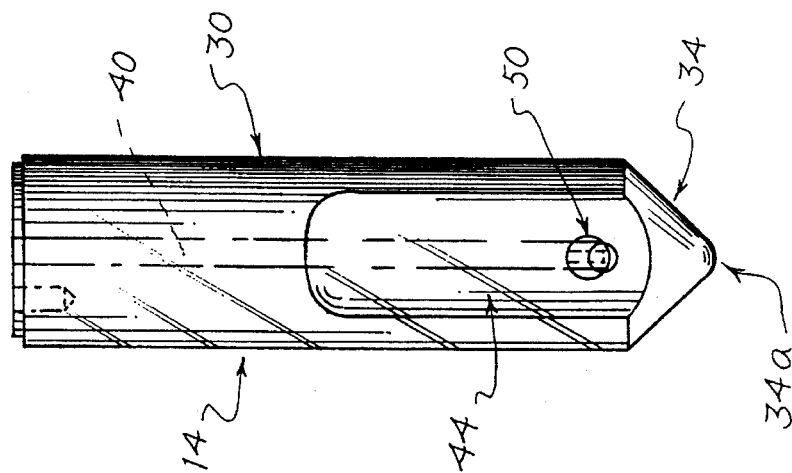
FIG. 3 illustrates a front view of the probe assembly shown in FIG. 2.
Figure 2:
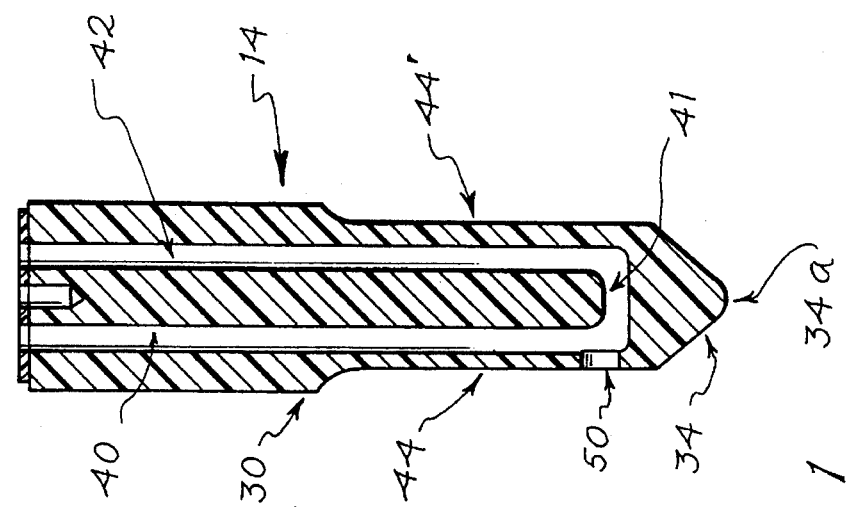
FIG. 2 illustrates a sectional view of a portion of the probe assembly shown in FIG. 1.

FIGS. 2 and 3 illustrate a side view and a front view, respectively, of count probe 14. The count probe 14 will be described below in detail.

The count probe 14 may be formed from separate sections bonded together by suitable means. The main body 30 is substantially cylindrical in shape while the tip section 34 is substantially conical with a substantially spherically shaped tip 34a. In an exemplary embodiment, some dimensions of the count probe 14 are:

Overall Length: 1.595 inches

Main body section 30 diameter: 0.425 inches

Substantially spherical tip 34a radius: 0.055 inches

Flats 44 and 44' are formed on an exterior surface of the main body section 30. The flats 44 and 44' are used to align the count wafer 54 with the opening 50.

Formed within and extending through the main body section 30 are two conduits 40 and 42. Opposite ends of conduits 40 and 42 align with other conduits (not shown) formed in the base 12. The depending ends of conduits 40 and 42 align with a substantially "U" shaped conduit 41 formed in the count probe 14.

Extending through a side wall of the count probe 14 and into the substantially "U" shaped conduit 41 is an opening 50. The opening 50 is properly dimensioned to mount a count wafer (not shown), which may be a synthetic sapphire or other gem stone. Specifically, in a preferred embodiment, the dimensions of the opening 50 are predetermined such that the corresponding dimensions of the count wafer are larger than the dimensions of the opening 50. Such a dimensional relationship can provide for an interference fit between the opening 50 and the has a diameter substantially about 0.863 inches and a center of the opening 50 is located about 0.010 inches from an open end or top of the substantially U-shaped conduit 41. In an exemplary embodiment, dimensional interference between the count wafer and the opening 50 is substantially within the range of about 0.0006" to about 0.0010". Larger dimensional interferences may generate sufficient stresses such that cracks may form in the probe 14.

The thickness of the wall through which the opening 50 is formed, in the illustrated embodiment, is about 0.041 inches. It has been found that a count wafer 54 (FIG. 5) can be mounted in the opening 50 and secured therein by forces exerted by the probe 14 to create an interference fit. The seal created by the interference fit should allow no more than about 100 nanoamps at about 9 Volts of electrical current leakage from the probe 14.

The forces exerted by the probe 14 to hold the count wafer 54 in place must be great enough to withstand pressure exerted on the count wafer 54 by the liquid flow system. The system typically exerts about 12 psi maximum pressure and about 3 psi maximum vacuum. The probe 14 is designed to withstand over about 100 psi of pressure or vacuum while still retaining the count wafer 54 at the opening 50 and maintaining the above-mentioned electrical properties (i.e., current leakage).

The fill flow geometry allows a rear side of the count wafer 54 to lie slightly out of the fill flow. Therefore, the fill flow is in contact with and can "wash" the rear side of the count wafer 54, thereby reducing the probability that bubbles might collect in the sensing region during analysis. Also, the fill flow geometry provides significant advantages to the probe 10 in that it helps to reduce the number of particles counted twice (recirculators) by controlling a jet of the fluid entering the count probe 14 through the count aperture. By positioning the count wafer 54 adjacent a side of the substantially U-shaped conduit 41, the jet of fluid through the count aperture contacts the channel wall on a side of the conduit 41 opposite from the count aperture.

FIG. 4 illustrates a front view of a count wafer 54 which may be mounted in the opening 50 of the count probe 14. FIG. 5 illustrates a cross-sectional view of the count wafer 54 shown in FIG. 4 taken along lines 6—6. In an exemplary embodiment, the dimensions of the count wafer 54 may be approximately as follows:

Outer diameter: 0.087 inches

Thickness: 0.025 inches

Concave recess 60 diameter: 0.060 inches

Figure 6:
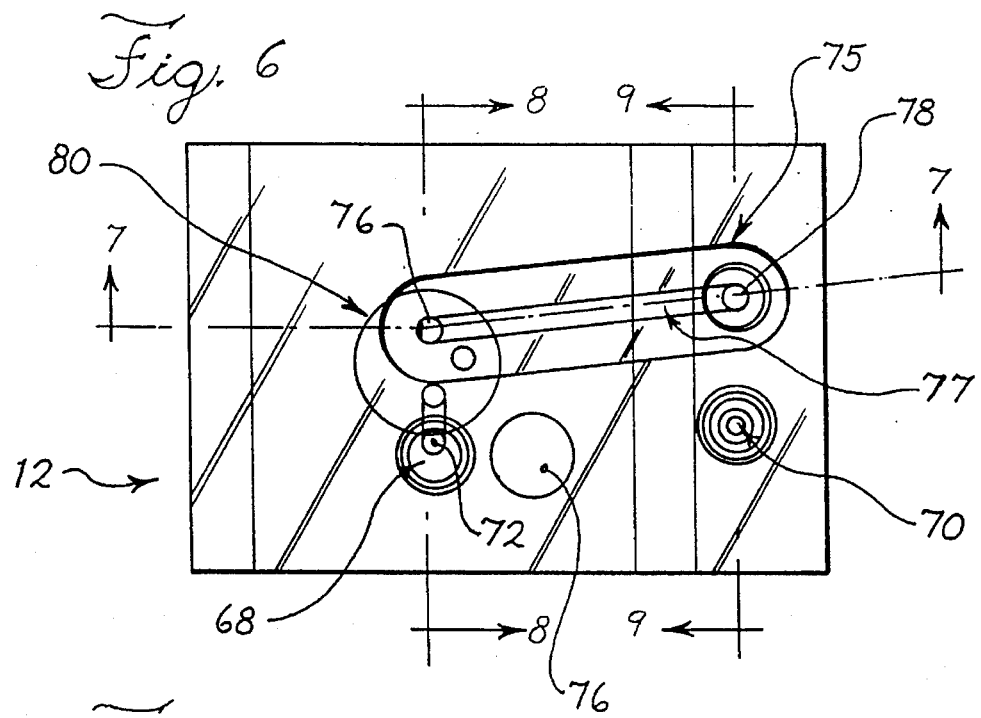
FIG. 6 illustrates a top view of base of the counting apparatus shown in FIG. 1.
Figure 8:
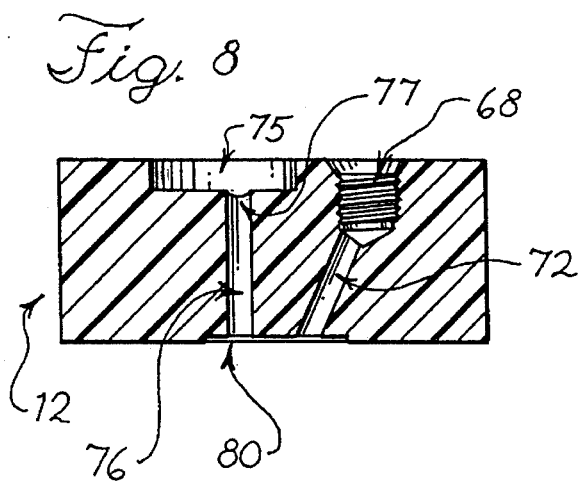
FIG. 8 is a cross-sectional view of base 12 of FIG. 6 taken along lines 9—9.
Figure 9:
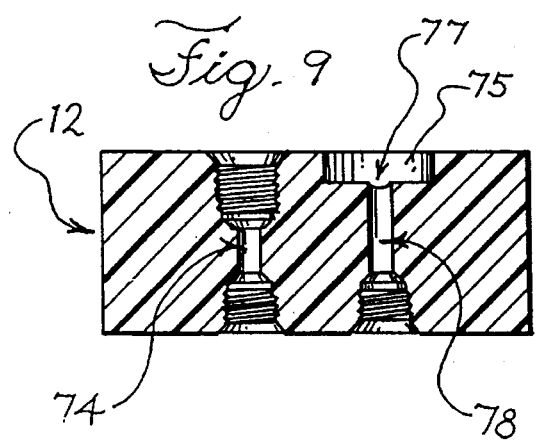
FIG. 9 is a cross-sectional view of base 12 FIG. 6 taken along lines 10—10.

Located at the center of the concave recess 60 is the count aperture 62 which extends through to the rear side or face 64 of the count wafer 54. The diameter of aperture 62 is chosen dependent upon the diameter of the cell type to be counted. In an exemplary embodiment, the count aperture 62 contained in the count wafer 54 may be chosen to have the following dimensions in the given situations:

Diameter of the count aperture 62 for red blood cells and platelets: about 45 micrometers Length of the count aperture 62 for red blood cells and platelets: about 60 micrometers Diameter of the count aperture 62 for white blood cells: about 100 micrometers Length of the count aperture 62 for white blood cells: about 70 micrometers The count, waste and fill probes 14, 16 and 18 are all connected to base 12 as illustrated in FIG. 1. FIGS. 6–9 illustrate the base 12 in greater detail. FIG. 6 illustrates a top view of the base 12. The base 12 is preferably formed of a solid acrylic block substantially rectangular in shape. Two ports 68 and 70 expose conduits 72 and 74 (see FIGS. 8 and 9) to the top surface of the base 12. The ports 68 and 70 allow the connection tubing 24 shown in FIG. 1 to communicate with conduits 72 and 74. The ports 68 and 70 are preferably threaded as shown in FIGS. 8 and 9 to allow the connection fitting 25 (see FIG. 1) to be threadibly engaged in place on the base 12. One end of the connection tubing 24 is then connected to the fitting 25. A third port 76 allows an electrode, not shown, and fluid to pass through the base 12. Unlike ports 68 and 70, port 76 may not be threaded. Other conduits may be formed in the base 12 and connections between those conduits and the rest of the probe assembly 10 will be better understood with reference to FIGS. 1 and 7–11.

Figure 7:
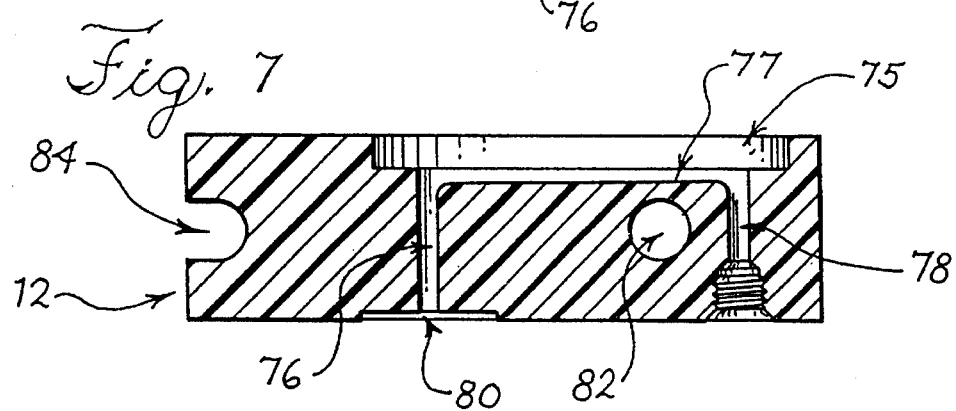
FIG. 7 is a cross-sectional view of base 12 of FIG. 6 taken along lines 8—8.

FIG. 7 is a cross-sectional view of the base 12 of FIG. 6 taken along lines 8—8. A substantially horizontal recess 75 is formed at the top of the base 12 including a conduit 77. Two conduits 76 and 78 extend vertically through the base 12 and are connected near the top of the base 12 by the horizontal conduit 77. Conduit 77 is illustrated in an "open" state. However, when the base plug (not shown) to be described with reference to FIGS. 10 and 11 is mounted in the recess 75 of the base 12, conduit 77 will be in a substantially "closed" state. In the closed state, the conduit 77 allows for connection with the conduits 76 and 78. The bottom of conduit 78 is preferably threaded to allow the fill probe 18 of FIG. 1 to be threadibly mounted on the base 12 in alignment with conduit 78. A recess 80 configured for facilitating mounting of the count probe 14 is formed on the bottom of the base 12. The recess 80 is positioned to align conduits 40 and 42 of the count probe 14 with conduits 76 and 72 (see FIG. 6) of the base 12, as will be described in detail hereinafter. An aperture 82 and "U" shaped recess 84 extend substantially horizontally through the base 12 to accommodate mounting of the probe assembly 10. Any appropriate system, such as automatic as well as manual systems, can be used to move the probe assembly 10 to various positions and locations.

FIG. 8 is a cross-sectional view of the base 12 of FIG. 6 taken along lines 9—9. Conduit 72 is angled towards conduit 76 so that both conduits communicate with recess 80. The count probe 14 is mounted in recess 80 so that conduit 40 of the probe 14 aligns with conduit 76 of the base 12 and conduit 42 of the probe 14 aligns with conduit 72 of the base 12, as shown in FIG. 12.

FIG. 9 is a cross-section view of the base 12 of FIG. 6 taken along lines 10—10. As previously described, conduit 78 aligns with conduit 77 in the base 12. The bottom of conduit 78 is preferably threaded so that the fill probe 18, shown in FIG. 1, can be threadibly mounted to base 12. Both end portions of conduit 74 are threaded so that the waste probe 16 can be connected to one end of conduit 74 and a connection fitting 25, shown in FIG. 1, can be connected to the opposite end of conduit 74. Connection tubing 24 can be connected to the connection fitting 25 to communicate with conduit 74.

FIGS. 10 and 11 illustrate a plan and a cross-sectional view, respectively, of the base plug 13. The plug 13 is configured to fit within the recess 75 formed in the top of the base 12, as shown in FIG. 1. Extending through the plug 13 is a conduit 86 which aligns with a recess 88 also formed in the plug 13. When the plug 13 is mounted in the recess 75 of the base 12, the recess 88 formed in the plug 13 cooperates with the conduit 77 formed in the base 12 to form a conduit connecting the conduits 76 and 78 in the base 12. When the plug 13 is mounted on the base 12, conduit 86 communicates with conduit 76 in the base 12. Conduit 76, in turn, communicates with conduit 40 of the count probe 14. In an exemplary embodiment, plug 13 is solvent bonded to the base 12. As shown in FIGS. 1 and 12, electrode 20 is inserted through conduit 86 in the plug 13 and extends through conduit 40 of the probe 14. When positioned for operation, the electrode 20 is located adjacent a distal opening of conduit 40 of tube 26 so that a distal end of the electrode 20 is adjacent opening 50. Conduit 86 is preferably substantially funnel-shaped so that a distal diameter of the conduit 86 is substantially smaller than the diameter of the remainder of the conduit 86. The electrode 20 has a diameter which is slightly smaller than the distal diameter of conduit 86. The adhesive may move along the electrode 20 towards the reduced diameter portion of conduit 86 to substantially reduce fluid leaking through conduit 86. The electrode 20 is preferably sealingly secured to the plug 13 by a suitable structure, such as an adhesive and the like. The adhesive may be a polymeric compound, such as Armstrong Epoxy A251 and the like.

FIG. 12 illustrates a cross-sectional view of a portion of the probe assembly 10 in use. The count probe 14 is shown at least partially submerged in a reservoir 15 containing a liquid suspension 17 of particles to be analyzed. Conduits 40 and 42 formed in the probe 14 are connected by conduit 41. The conduits are typically of a constant diameter of about .060 inches.

As previously described, conduit 40 is connected with conduit 76 in the base 12 and thus is connected by conduit 77 to conduit 76, which is connected to the fill probe 18. In addition, electrode 20 is positioned in conduit 40 through conduits 86 and 76 of the base plug 13 and base 12, respectively. The conduit 42 of the count probe 14 communicates with connection tubing 24 through conduit 72 of the base 12.

A further understanding of the construction of the probe assembly, as well as an appreciation of the steps comprising embodiments of the methods of the present invention, may be gained through an understanding of the operation of the probe assembly. Referring to both FIGS. 1 and 12, the operation of the particle analyzer will now be described.

During the counting phase of the analytical cycle a vessel, which may have a sample and a reagent reservoir, is positioned to at least partially submerge the probes 14, 16 and 18 of assembly 10 in the fluids contained in the vessel. A suitable vessel is described in U.S. patent application, Ser. No. 07/482,007 entitled "Self-Filling, Anti-Siphon Fluid Flow System for Particle Analysis Instruments and a Disposable Reagent Pack for use Therewith", filed Feb. 16, 1990, which is incorporated herein by reference. Other vessels may also be appropriate.

Once the probes 14, 16 and 18 of assembly 10 have been sufficiently submerged in the fluids contained in the vessel, the analytical cycle of the system may be started. In an exemplary embodiment, both the fill and waste probes 18 and 16 have apertures 19 and 17 respectively, (see FIG. 1) which are approximately 203 micrometers in diameter. Fluid enters through the fill aperture 19 in the fill probe 18 from the reagent reservoir. This fluid movement may be generated by a suitable mechanism, such as a fluid displacement mechanism pulling at a constant flow rate and the like. The reagent solution is supplied to conduit 40 of the count probe 14 through conduits 77 and 78 where the reagent solution mixes with the sample liquid. Suspended particles enter through the count aperture 62 of the count wafer 54. A voltage potential is applied between electrode 20 placed in conduit 40 of the count probe 14 and electrode 22 disposed in the sample reservoir 15 to cause a current to flow through the adjacent fluid. Appropriate electronics (not shown) are provided for detecting a change in voltage when a cell passes through the count aperture 62 of the count wafer 54. Each passing cell causes an electronically recorded cell count to increase. The constant flow rate displacement mechanism generates a negative pressure in conduit 40 of the count probe 14 and fill aperture 19. The negative pressure is predetermined such that a desired rate of fluid flow is maintained through the count aperture 62. As particles enter the count probe 14 through the count aperture 62, they mix with the fluid flowing in conduit 40 thereby causing the particles to flow around the conduit 41.

During the count phase, a valve, not shown, is activated to prevent fluid from entering through the waste aperture 17 in the waste probe 16. When the counting phase is complete, flow is reversed, for example, by reversing the constant flow rate displacement mechanism (not shown). The fluid displacement mechanism collects the diluted sample. The displacement mechanism then expels the collected sample back out the probe assembly 10 to the reagent reservoir before accessing the next sample. Preferably, the expel cycle delivers waste out the probe assembly 10 at approximately twice the flow rate of the sampling cycle. Waste leaves the probe assembly 10 through the waste probe 16 the fill probe 18 and the Count aperture 62. Then, the valve to the waste probe 16 is closed. Therefore, the flow rate out of the fill probe 18 and the count aperture 62 is increased by a factor, preferably about two. These steps substantially clean the apertures of any debris. For red blood cell and platelet counting, the fill, count and waste apertures may have diameters, for example of 203, 45, and 203 micrometers, respectively. For white cell counting, the same diameters may be, for example, 203, 100 and 203 micrometers, respectively.

With constructions of exemplary embodiments of the probe assemblies which may be manufactured according to methods of the present invention being thusly described in detail, the steps comprising embodiments of the methods of the present invention will now be discussed in detail. It is to be remembered that these methods may be utilized to construct articles other than those described herein.

To manufacture and construct a particle analyzer having a count probe for counting particles, such as cells and the like, a substantially tubular or core member is formed. The core member may be made from any suitable polymeric material, as disclosed above, by an appropriate polymer manufacturing technique, such as molding, extruding and the like.

In an exemplary embodiment, the core member is constructed from cast acrylic or similar polymer. If the acrylic material were provided in a sheet form, then the sheet should be subjected to a "shrinking cycle" before it is fabricated. The shrinking cycle may relieve inherent stresses induced in the material during casting. The shrinking cycle may be performed in a convection-type oven. The raw acrylic to be "shrunk" is placed in the oven on a substantially smooth surface, such as a piece of glass, aluminum, and the like, in a disposition such that air can flow freely around the acrylic. The temperature in the oven is ramped directly to about 152 degrees Celsius. This temperature is maintained for about 7 hours. After that time period, the oven is allowed to cool to ambient temperature while the acrylic is still inside.

It is to be noted that if the raw acrylic sheet is less than about 6 mm thick, then the acrylic sheet should not be shrunk, as described above, but should be annealed. The same is true if the raw acrylic stock were provided in rod form. Further, if the raw acrylic were provided in a black or white cast sheet form, then the raw acrylic should be annealed.

Figure 13:
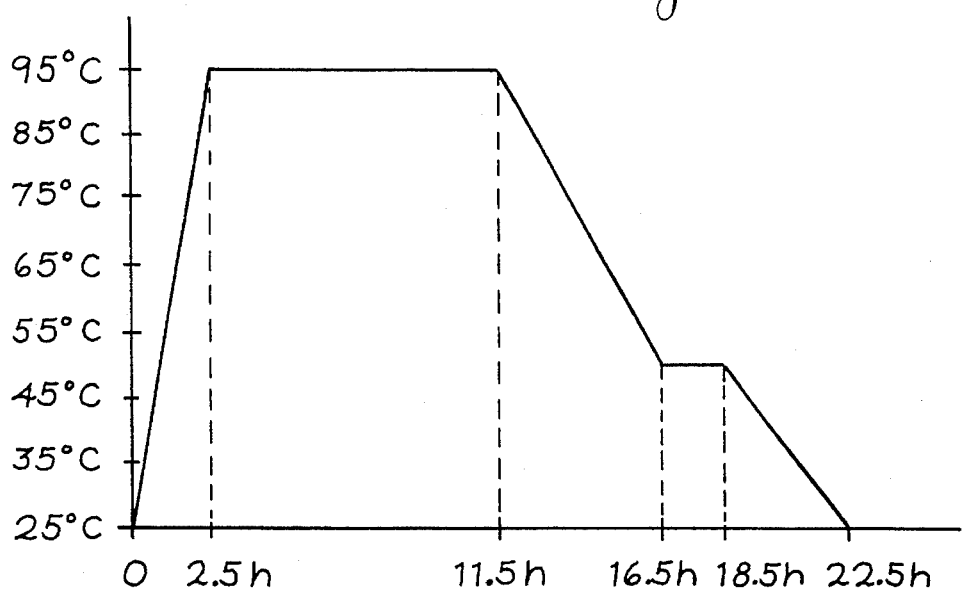
FIG. 13 is a temperature profile followed during construction of the count probe according to an embodiment of the method of the present invention.

Annealing of the raw acrylic takes place as follows (FIG. 13). The raw acrylic is placed into a convection oven as before. The temperature within the oven is thermally moved or ramped up from ambient temperature to about 95 degrees Celsius in about two and one half hours. The acrylic is then thermally stabilized at about 95 degrees Celsius for about nine hours. After that time, the temperature is moved or ramped down to about 50 degrees Celsius in about 5 hours, and the acrylic is thermally stabilized at that temperature for approximately 2 hours. Finally, the temperature is ramped down to ambient temperature in about 4 hours.

After the acrylic has been appropriately annealed or shrunk, by the processes described above, the acrylic is ready for fabrication into a count probe. The acrylic is formed generally into the core member. Appropriate fluid passages are formed in the acrylic along with other structures described above by a suitable technique. The opening for the count wafer is machined with an appropriate surface finish such that a seal with the above described properties, i.e. current leakage, may be formed between the core member and the count wafer. Because of the above-discussed processes, the acrylic is substantially stress free and is ready to accept the count wafer.

The count wafer is applied to the opening in the acrylic core member. The count wafer preferably is positioned below an outer surface of the acrylic core member a distance sufficient to approximately center the count wafer in the opening 50. In an exemplary embodiment, this distance measures about 0.005". Because of the above-discussed dimensional interferences, an interference fit is formed between the core member and the count wafer. The interference fit may generate stresses in the core member.

Once the count wafer is applied to the opening in the core member, the interference-fitted assembly should undergo an annealing method as soon as possible. This annealing method can relieve most of the stresses in the assembly. Some stresses may remain because the count wafer may maintain a force on the probe. One possible annealing method, which may also be used as a shrinking cycle, utilizes a temperature profile illustrated in FIG. 13. As shown, the assembly is placed in a convection oven, as described above, and the temperature is ramped up to about 95 degrees Celsius in about two and one half hours. The assembly is maintained at that temperature for about nine hours. At the end of that nine hours, the temperature is ramped down to about 50 degrees Celsius in about five hours. The assembly is maintained at about 50 degrees Celsius for about two hours. Then, the oven, with the assembly inside, is allowed to cool to the ambient temperature in about four hours. Once the assembly has cooled to ambient temperature, it is ready for further assembly with the remainder of the instrument because the annealing method has relieved substantially all of the stresses in the assembly.

Another method, according to the teachings of the present invention, for making a stress relieved count probe will be described with reference to FIG. 14. This method, for the sake of clarity, will be referred to as the heat insert method. The heat insert method is substantially similar to the method described immediately above except for the differences outlined below. The heat insert method will be described with respect to an acrylic core member to facilitate understanding. It is to be noted, however, that the heat insert method, as well as all of the other methods described herein, may be employed, with suitable modifications, with core members comprising different materials.

In the heat insert method, the core member is prepared as described earlier such that it is substantially stress free. The core member is ready for the count wafer. Before the count wafer is applied to the core member, the core member is heated, as shown in FIG. 14, to a temperature just below a transition temperature of the core member material. In an exemplary embodiment, the acrylic core member is heated to a temperature just below the acrylic's glass transition temperature which is substantially within the range of about 85 degrees Celsius to about 95 degrees Celsius. For the sake of clarity, the transition temperature is assumed to be just above 85 degrees Celsius in FIG. 14. While the core member is at this temperature, the count wafer is inserted as described above, i.e. located below the outer surface of the core member a distance of about 0.005 inches.

Figure 14:
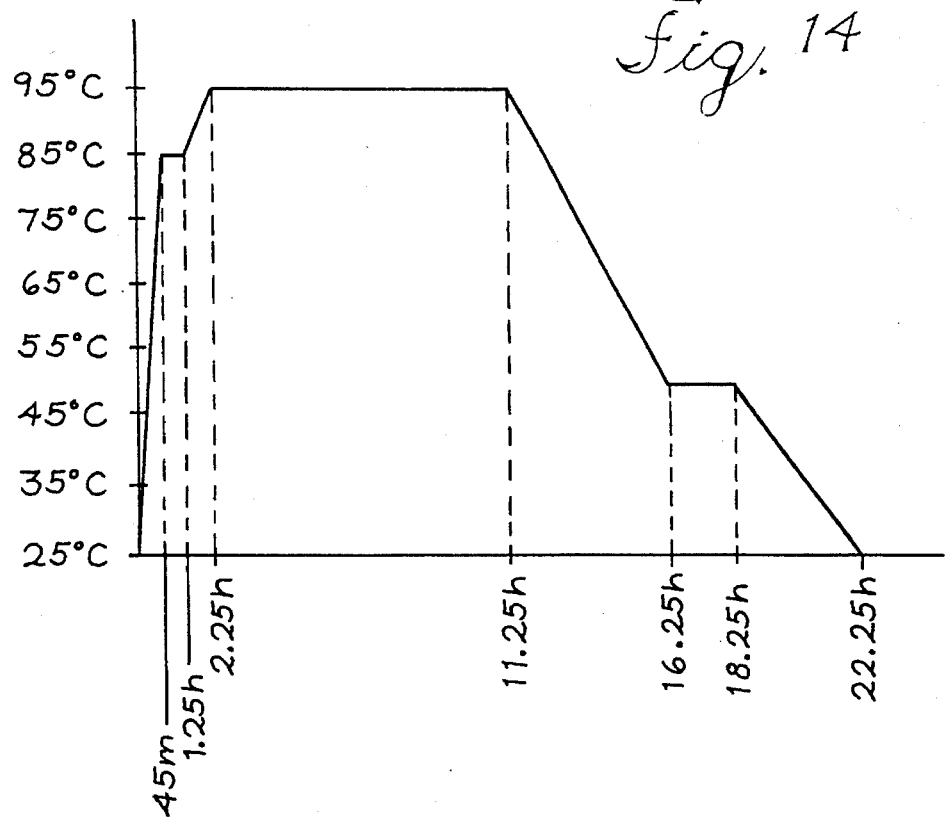
FIG. 14 is another temperature profile which may be used to manufacture a count probe according to the herein discussed methods.

Once the count wafer is applied to the core member, the assembly comprising the core member and the count wafer is annealed by utilizing the temperature profile illustrated in FIG. 14. Specifically, the temperature of the assembly is maintained at about 85 degrees Celsius for about thirty minutes. Then, the temperature is ramped up from about 85 degrees Celsius to about 95 degrees Celsius in about one hour. The temperature is maintained at about 95 degrees Celsius for about nine hours. After about 9 hours at about 95 degrees Celsius, the temperature is ramped down to about 50 degrees Celsius in about five hours. The assembly is maintained at about 50 degrees Celsius for about two hours. After that, the temperature is ramped down to ambient temperature in about four hours. Once this process is completed, it is desirable to anneal the assembly a second time, again using the temperature profile illustrated in FIG. 13.

Another method of making a stress relieved count probe will be discussed with reference to FIG. 15. This method will be referred to as the hot form method for the sake of clarity. The hot form method is substantially similar to the two last discussed methods except for the differences outlined below.

The core member and the count wafer are prepared as before. To provide for the desired properties, i.e. current leakage, portions of the acrylic core member, specifically the opening for receiving the count wafer, should preferably have a diamond cut surface, and the count wafer should preferably have a polished surface. This preparation of the count wafer and the opening in the core member can further facilitate manufacture of a count probe having the intended properties. The core member is made substantially stress free prior to count wafer insertion and the count wafer is applied below the surface of the core member, preferably by about 0.005 inches.

Figure 15:
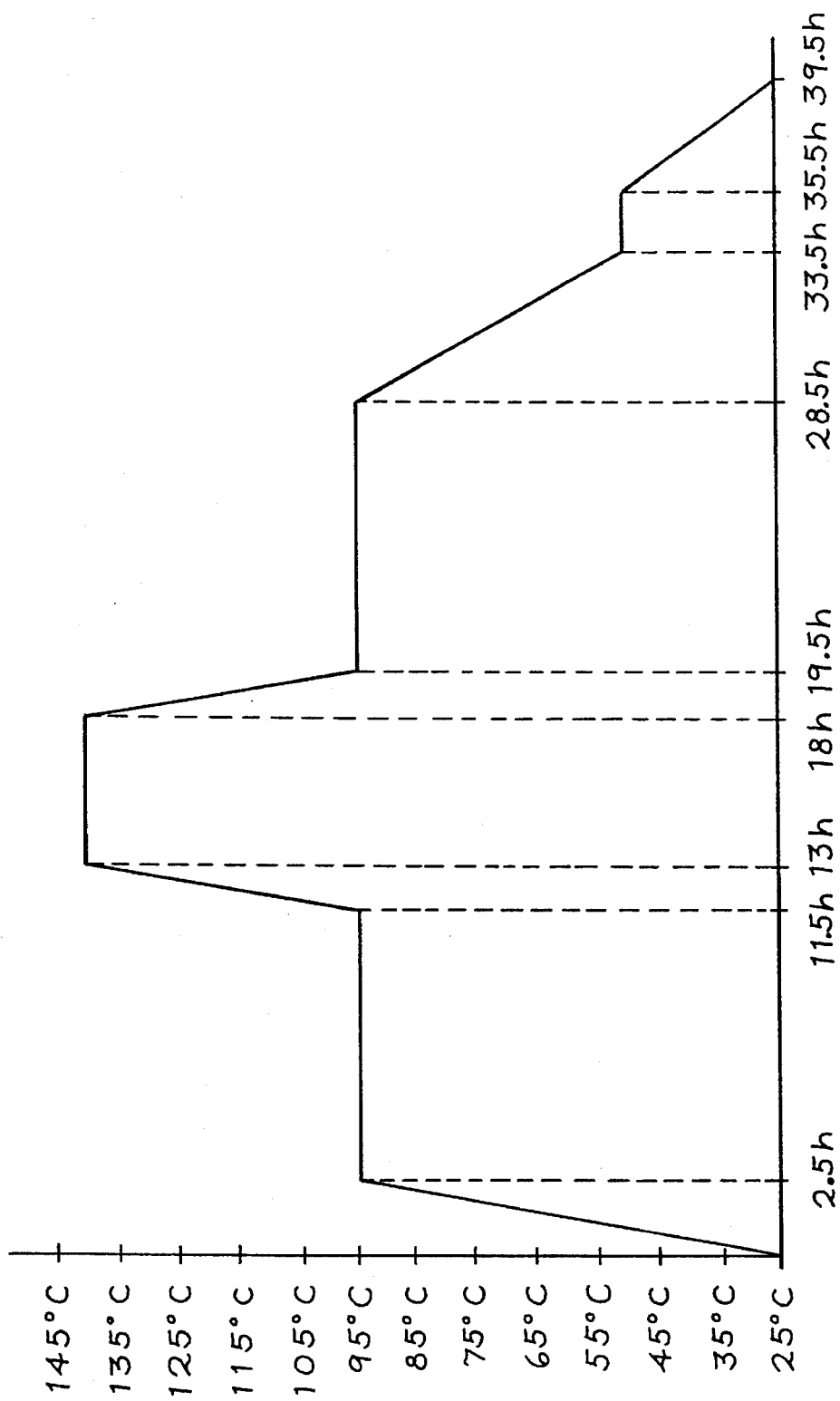
FIG. 15 is yet another temperature profile which may be used to construct a count probe in accordance with teachings of the methods of the present invention.

Once the count wafer is applied to the core member, the assembly undergoes an annealing method utilizing the temperature profile illustrated in FIG. 15. The assembly is introduced to the convection oven as before. The temperature of the assembly is ramped up to about 95 degrees Celsius in about two and one half hours. The assembly is kept at about 95 degrees Celsius for about nine hours. The temperature is ramped up to about 140 degrees Celsius in about one and one half hours, and maintained at that temperature for about 5 hours. The temperature is then ramped down to about 95 degrees Celsius in about one and one half hours and maintained at that temperature for about 9 hours. Then, the temperature is ramped down to about 50 degrees Celsius in about 5 hours and held at that temperature for about 2 hours. The temperature of the assembly is then ramped down to ambient temperature in about 4 hours. The assembly is now ready for further manufacture.

The annealing methods discussed above substantially reduce stress present within the assembly. The shrinking or annealing processes performed before application of the count wafer to the core member can substantially relieve substantially all of the stresses present in the core member and thus in the count probe. The annealing methods performed after application of the count wafer to the core member substantially reduce stress generated by the interference fit formed between the count wafer and the core member. It is to be remembered that performance of any of these methods, alone or in combination, can result in production of a stress relieved count probe or a count probe whose stresses are reduced to an acceptable level. Also, the count wafer may not necessarily be removable from the core memeber after an annealing method has been performed. However, the entire core member, including the count wafer, may be removable from the remainder of the probe assembly. By removing and replacing the entire core member, the count wafer may be exchanged or replaced. Additionally, it is to be understood that steps from one method can be mixed with steps from another method without departing from the scope of the embodiments of the invention.

Other modifications of these methods are also possible without departing from the scope of the invention. For instance, the methods may be employed, sometimes with suitable modifications, with materials other than acrylic. Also, the methods may be combined in any suitable fashion.

What is claimed is:

1. A method of making a count probe for counting particles, the method comprising the steps of:
   (a) forming a count wafer;
   (b) forming a core member having an opening for accepting the count wafer;
   (c) applying the count wafer to the opening in the core member while the core member is at ambient temperature to form an interference fit between the count wafer and the core member; and
   (d) annealing the core member after application of the count wafer to the opening in the core member to relieve substantially all stress in the core member but leaving sufficient stress such that the count wafer is retained with the core member by an interference fit, the annealing step comprising
       (i) changing the core member from ambient temperature to a first temperature within a first time period;
       (ii) maintaining the core member at the first temperature for a second time period;
       (iii) changing the core member to a second temperature within a third time period;
       (iv) maintaining the core member at the second temperature for a fourth time period;
       (v) changing the core member to a third temperature within a fifth time period;
       (vi) maintaining the core member at the third temperature for a sixth time period; and
       (vii) changing the core member to ambient temperature within a seventh time period.

2. A method of making a count probe for counting particles, the method comprising the steps of:
   (a) forming a count wafer;
   (b) forming a core member having an opening for accepting the count wafer;
   (c) applying the count wafer to the opening in the core member while the core member is at ambient temperature to form an interference fit between the count wafer and the core member; and
   (d) annealing the core member after application of the count wafer to the opening in the core member to relieve substantially all stress in the core member but leaving sufficient stress such that the count wafer is retained with the core member by an interference fit, the annealing step comprising (i) changing the core member from ambient temperature to a first temperature within a first time period;
(ii) maintaining the core member at the first temperature for a second time period;
(iii) changing the core member to a second temperature within a third time period;
(iv) maintaining the core member at the second temperature for a fourth time period;
(v) changing the core member to a third temperature within a fifth time period;
(vi) maintaining the core member at the third temperature for a sixth time period;
(vii) changing the core member to a fourth temperature within a seventh time period;
(viii) maintaining the core member at the fourth temperature for an eighth time period; and
(ix) changing the core member to ambient temperature within a ninth time period.

* * * * *